United States Patent [19]

Lowe

[11] 3,954,800

[45] May 4, 1976

[54] OXIDATION OF THIOLS TO DISULFIDES

[76] Inventor: Orville G. Lowe, 3815 Los Feliz Blvd., Los Angeles, Calif. 90027

[22] Filed: Dec. 26, 1973

[21] Appl. No.: 427,470

[52] U.S. Cl............................ 260/327 R; 260/332.8; 260/453 RZ; 260/545 R; 260/608
[51] Int. Cl.²......................................... C07D 339/08
[58] Field of Search......... 260/327 R, 332.8, 545 R, 260/608, 453 R

[56] References Cited
UNITED STATES PATENTS

| | | | |
|---|---|---|---|
| 3,376,313 | 4/1968 | Wallace | 260/327 |
| 3,428,671 | 2/1969 | Toland | 260/513 |
| 3,513,088 | 5/1970 | Karabinos et al. | 208/189 |

*Primary Examiner*—Henry R. Jiles
*Assistant Examiner*—C. M. S. Jaisle
*Attorney, Agent, or Firm*—George F. Smyth

[57] ABSTRACT

A process for oxidizing alkyl thiols, cycloaliphatic thiols and aralkyl thiols or mixtures thereof to disulfides. The thiol reactant is oxidized by a sulfoxide reactant in the presence of a halogen-hydrogen halide catalyst. The catalysts for the reaction are iodine, hydrogen iodide, bromine, hydrogen bromide, chlorine, hydrogen chloride and mixtures thereof.

23 Claims, No Drawings

OXIDATION OF THIOLS TO DISULFIDES

Dimethyl sulfoxide and related sulfoxides are known oxidizing agents. For example, in U.S. Pat. No. 3,376,313, organic sulfoxides have been described for use in conjunction with an organic amine or acid to oxidize organic thiols to organic disulfides.

In investigating the use of a sulfoxide as an oxidizing agent in the production of disulfides from thiols, I have discovered that certain halogens and hydrogen halides are excellent catalysts for the oxidation reaction. Except in the oxidation of aromatic thiols, the use of halogen-hydrogen halide catalysis is markedly superior to ordinary acid catalysis. Thus, the present process is directed to the oxidation of specified thiols with a sulfoxide in the presence of a halogen-hydrogen halide catalyst to produce a disulfide. The halogen or hydrogen halide catalysts which may be employed are iodine, bromine, chlorine, hydrogen iodide, hydrogen bromide, hydrogen chloride, or mixtures thereof. Fluorine and hydrogen fluoride have been found to be relatively ineffective as catalysts and, thus, are not included within the above definition of catalytic materials.

In accord with the present process, the oxidation procedure is carried out by reacting the thiol with the sulfoxide, preferably in stoichiometric excess, in the presence of an effective amount of the halogen-hydrogen halide catalyst. Also, the reaction can be carried out in the presence of an inert solvent. The process is carried out at a temperature less than about 100°C. under conditions which avoid the presence of gross amounts of water that have been found to retard the reaction. The control of the reaction temperature below about 100°C. serves to prevent the undesired further oxidation of the disulfide product to form materials such as sulfonic acids.

Although not bound by any theory, the present oxidation process may be discussed in terms of the following generalized reactions:

I. $2R\text{—}SH + X_2 \rightarrow R\text{—}SS\text{—}R + 2HX$

II. $2HX + R'\text{—}\underset{\underset{O}{\|}}{S}\text{—}R'' \rightarrow X_2 + H_2O + R'\text{—}S\text{—}R''$ In the above reactions, R may be an alkyl group, an aralkyl group, or a cycloaliphatic group such as methyl, ethyl, isopropyl, n-pentyl, t-butyl, cyclohexyl, benzyl, and the like. When R is an alkyl, the R group may contain from 1 to about 20 carbon atoms; when R is a cycloaliphatic group, it may contain from 3 to about 20 carbon atoms, and when R is an aralkyl group, the R group may contain from 5 to about 20 carbon atoms, e.g., thenyl, furfuryl, benzyl, phenylethyl, phenylpropyl and the like. Also, the —SH group may be linked to the R group through a carbonyl, i.e.,

and a mixture of R—SH reactants may also be employed to produce disulfides containing mixed R groups or mixed

groups.

R is preferably free from olefinic or acetylenic unsaturation, and, in addition, R may include substituent groups which are unreactive under the conditions of the process, e.g., carbonyl, nitro, carboxylic acid groups, and the like. R may also be substituted with one or more thiol groups. The process will then provide oxidation of the several thiol groups to produce cyclic products, e.g., a cyclic disulfide dimer, or other polymers depending on the size and nature of the R group and the specific reaction conditions.

The groups denoted as R' and R'' in the above equations are lower alkyl groups such as methyl, ethyl, isopropyl, and the like. R' and R'' may be either the same or different and may be bonded together to form a ring structure as in the case of tetramethylene sulfoxide. As indicated a reaction product which results through reduction of the sulfoxide is a sulfide in which R' and R'' may each be bonded to a sulfur atom.

X, as indicated in the reactions I and II, is iodine, bromine, or chlorine. Similarly, HX in the above reactions may be hydrogen iodide, hydrogen bromide, or hydrogen chloride.

As indicated in the reactions, water is a reaction product and, thus, its presence in the reaction mixture cannot be avoided. However, it has been found that the presence of water slows down the course of the reaction and, thus, the presence of gross quantities of water should be avoided. To decrease the content of water in the reaction mixture, it is, therefore, desirable to avoid the use of reactants and catalysts which contain excess amounts of water. In addition, the water concentration in the reaction mixture can be reduced by keeping the level of the thiol reactant at a moderate level with respect to the sulfoxide. Thus, the weight and volume of the water will be relatively low with respect to the weight and volume of the sulfoxide.

When the present process is conducted on a large scale, the water which is formed in the reaction may be continuously removed, for example, by absorption from the reaction mixture, distillation under reduced pressure if necessary, or by bubbling air through the reaction mixture to evaporate water into the air stream.

In terms of catalytic effect, it has been found that on a molar basis chlorine and hydrogen chloride have the least catalytic activity, with bromine and hydrogen bromide having the greatest catalytic activity, and iodine and hydrogen iodide having an intermediate catalytic activity. Additionally, it has been found that a mixed catalyst using trace amounts of iodide or hydrogen iodide in combination with chlorine or hydrogen chloride as the primary catalyst greatly enhances the catalytic effect of the chlorine or hydrogen chloride.

A convenient means for monitoring the course of the reaction is the intense color produced by iodine in the presence of excess sulfoxide. This color disappears on addition of the thiol reactant to the reaction mixture but the color reappears, usually over a period of several minutes, when the oxidation of the thiol to the disulfide is complete.

Similarly, bromine gives yellowish solutions in the presence of sulfoxides and the yellowish color is removed by addition of thiol reactant. It has, however, been observed that the yellowish color reappears on completion of the oxidation of the thiol reactant to a disulfide. The bromine color is much less intense than the iodine color and, thus, is less satisfactory as an indicator for the completion of the oxidation reaction.

No color change was observed in the use of a chlorine —HCl catalyst. However, the lack of a color change on completion of the oxidation reaction in use of a chlorine —HCl catalyst may be overcome by the addition of a trace amount of iodine or HI to the reaction mixture. Also, the course of the reaction may be followed by periodically withdrawing a small quantity of the reaction mixture, such as a drop and adding this to a small quantity of a dilute solution of iodine in sulfoxide. When the iodine color persists in the test solution, this is an indication that the oxidation is essentially complete.

In the performance of my process, the sulfoxide reactant is preferably employed in a molar excess of about 100 percent with respect to the thiol groups in the thiol reactant. The halogen-hydrogen halide catalyst is present in a catalytically effective amount. In my experiments, catalyst concentrations of about 1.4 to 1.6 mole percent (moles/100 moles) of the sulfoxide were found satisfactory. However, other catalyst concentrations may be used and an effective amount of catalyst for any particular oxidation may be determined readily by running the oxidation at several catalyst concentrations to determine the optimum concentration. When the catalyst is the halogen $X_2$, the catalyst concentration was calculated in terms of hydrogen halide equivalents.

In the case of mixed chlorine-hydrogen chloride:iodine-hydrogen iodide catalysis, the HCl catalyst or the $Cl_2$ catalyst calculated as equivalents of HCl catalyst was generally employed at 0.9 to 1.0 mole percent of the sulfoxide reactant and iodine or HI, calculated as HI equivalents, was generally present at a concentration of about 0.06 to about 0.07 mole percent with respect to the sulfoxide reactant.

To further illustrate the process of the invention, there are presented the following examples. In the examples, the dimethyl sulfoxide (DMSO), halogens, hydrohalic acids, hydrofluoric acid, nitric acid, and sulfuric acid were reagent grade and the tettramethylene sulfoxide and dipropyl sulfoxide were dried over molecular sieves and distilled. The concentration of the acids in weight percent was as follows unless otherwise indicated: HI, 57%; HBr, 48%; HCl, 37%; HF, 48%; $HNO_3$, 70%, and $H_2SO_4$, 96%. The methanesulfonic acid was redistilled, and, thus, was substantially 100% acid. The thiol reactants which were commercial thiols were used directly while those of practical or technical grade were first purified by suitable means.

EXAMPLE I

In a number of separate experiments, set forth in Tables I–III, which follow, a mixture of 2-methyl-2-propanethiol with dimethyl sulfoxide, catalyst and any added water was heated at a temperature of 65°C. In these experiments, the mole ratio of the thiol to the sulfoxide was 0.41, except where otherwise indicated. The amount of the sulfoxide reactant was generally 0.1 to 0.13 gram moles and, the concentration of the catalyst is shown in the Tables as moles per 100 moles of sulfoxide (mole percent). When the catalyst was a halogen, the halogen concentration is expressed in terms of equivalents of hydrohalic acid.

The completion times for the reactions were determined by periodically withdrawing a drop of the reaction mixture, in the event that the reaction mixture did not contain iodine, with the reaction mixture then being added to 1 milliliter of a 0.025 percent solution of iodine in dimethyl sulfoxide (weight/volume). This procedure was continued using new portions of test solution until no decolorization occurred which indicated completion of the reaction. When the reaction mixture included an iodine-containing catalyst, the reaction was continued until the in situ reappearance of the iodine color, unless otherwise indicated.

As the oxidation reactions progressed, the disulfide product formed a second liquid phase and, when the reaction was completed, the iodine color reappeared in the lower sulfoxide phase when the iodine-containing catalyst was employed. In the reactions which did not employ an iodine-containing catalyst, the no-decolorization test, e.g., withdrawal of a drop of the reaction mixture, etc., was applied to both of the liquid phases for preparation of test data.

The iodine color appearance (where an $I_2$-HI catalyst is present in the reaction mixture) and the no-decolorization test yield slightly different results in regard to completion time. Iodine color does not appear until all the thiol reactant is gone and iodine was reformed. However, the iodine color persists in the no-decolorization test when there is insufficient thiol to remove the iodine which occurs when about 98 to 99 percent of the thiol reactant has been oxidized using the indicated iodine concentration. Thus, the oxidation is completed sooner when gauged by the no-decolorization test than when gauged by the in situ iodine color formation where iodine is used in the catalysis.

In the results shown in Table I–III, the designation $Inc_n$ indicates an apparent reaction as shown by separation of product but with the reaction otherwise being incomplete in $n$ hours. The designation $NAR_n$ indicates that there was no apparent reaction in $n$ hours as indicated by the formation of a separate liquid phase.

TABLE I

| Oxidation of 2-methyl-2-propanethiol to Bis(t-butyl) disulfide by DMSO | | | |
|---|---|---|---|
| Experiment Number | Catalyst | Cat. Concen. | Completion Time (hours.) |
| 1 | $I_2$ | 1.24 | 2.3 |
| 2 | $I_2$ | 1.36 | 1.7* |
| 3 | $I_2$ | 1.36 | 2.0 |
| 4 | $I_2$ | 1.36 | 1.9** |
| 5 | $I_2$ | 2.48 | 0.3 |
| 6 | HI | 1.37 | 3.5 |
| $a_7$ | $Br_2$ | 0.48 | 4.8 |
| $b_7$ | $Br_2$ | 0.72 | 1.7 |
| 7 | $Br_2$ | 1.44 | 0.2 |
| 8 | HBr | 0.91 | 1.8 |
| 9 | HBr | 1.40 | 0.8 |
| 10 | HCl | 1.42 | $Inc_7$ |
| 11 | HCl | 2.84 | 8.0 |
| 12 | HCl | 1.42 | 4.5*** |
| 13 | HF | 1.42 | $NAR_7$*** |
| 14 | $CH_3SO_3H$ | 1.39 | $NAR_7$*** |
| 15 | $HNO_3$ | 1.42 | $NAR_7$*** |

*Completion determined by the no-decolorization test.
**Oxidation conducted under a nitrogen atmosphere.
***Mole ratio of thiol to DMSO, 0.205.

As shown by the data in Table I, the completion time of the reaction was dependent upon both the nature of the catalyst and also on the catalyst concentration. The bromine-hydrogen bromide catalysis was found to be most effective and was followed by iodine-hydrogen iodide catalysis, and then by hydrogen chloride catalysis. Also, it was found that an increased concentration of the halogen-hydrogen halide catalyst caused a reduction in the reaction time. Experiments 13–15 indicate that acids, in general, did not have any discernible catalytic effect upon the desired oxidation of the thiol to the disulfide.

In experiment number 2, the no-decolorization test was used to determine completion time even though the reaction mixture contained iodine catalyst. As would be expected, the completion time indicated was somewhat less than that indicated in experiment 3 (using the same reaction conditions as experiment 2) where iodine color appearance was used to determine completion time.

TABLE II

Mixed Catalysis, Oxidation of 2-methyl-2-propanethiol to Bis(t-butyl) disulfide by DMSO

| Experiment Number | Principal Catalyst (conc) | Enhancer Catalyst (conc) | Completion Time (hrs.) |
|---|---|---|---|
| 10 | HCl (1.42) | none | Inc$_7$ |
| 16 | HCl (0.95) | $I_2$ (0.067) | 0.8 |
| 8 | HBr (0.91) | none | 1.8 |
| 17 | HBr (0.91) | $I_2$ (0.063) | 1.5 |
| 18 | $H_2SO_4$ (1.13) | $I_2$ (0.062) | NAR$_3$ |
| 19 | $CH_3SO_3H$ (1.40) | $I_2$ (0.065) | NAR$_5$ |
| 20 | HF (1.42) | $I_2$ (0.070) | NAR$_7$* |
| 21 | $I_2$ (0.62) | $CH_3SO_3H$ (0.73) | 6.8 |
| 1 | $I_2$ (1.24) | none | 2.3 |
| 22 | $I_2$ (1.24) | $CH_3SO_3H$ (1.40) | 1.0 |
| 5 | $I_2$ (2.48) | none | 0.3 |
| 12 | HCl (1.42) | none | 4.5* |
| 23 | HCl (1.42) | $CH_3SO_3H$ (1.40) | 3.0* |

*Mole ration of thiol to DMSO, 0.205.

The data in Table II illustrates the benefits which may be obtained through use of a mixed catalyst system. As shown, the presence of a small quantity of iodine provided a substantial increase in the effectiveness of hydrochloric acid as a catalyst and also produced a small increase in the effectiveness of hydrobromic acid as a catalyst. However, the presence of a small amount of iodine in conjunction with acids such as sulfuric acid, methane sulfonic acid and hydrofluoric acid had no discernible beneficial effect.

The data in Table II also demonstrates that an increase in the acidity of the reaction system, when coupled with the use of a halogen-hydrogen halide as the principal catalyst, did produce a beneficial effect. However, this effect was less marked than that produced by merely increasing the concentration of the halogen-hydrogen halide catalyst.

TABLE III

Effect of Water, Oxidation of 2-methyl-2-propanethiol to Bis(t-butyl) disulfide by DMSO

| Experiment Number | Catalyst (conc) | Water (conc) | Completion Time (hrs.) |
|---|---|---|---|
| 3 | $I_2$ (1.36) | nil | 2.0 |
| 24 | $I_2$ (1.36) | 7.45 | 3.5 |
| 6 | 57% HI (1.37) | 7.36 | 3.5 |
| 7 | $Br_2$ (1.44) | nil | 0.2 |
| 25 | $Br_2$ (1.44) | 6.78 | 0.8 |
| 9 | 48% HBr (1.40) | 6.74 | 0.8 |
| 26 | 24% HBr (1.40) | 15.5 | 2.0 |

The data set forth in Table III demonstrates that water has an adverse effect upon the rate of the oxidation reaction. The water content of the reaction mixture is expressed in Table III in terms of mole percent of the sulfoxide reactant.

Experiment number 26 illustrates, however, that a substantial amount of water can be tolerated while still having a reasonable reaction rate. Thus, even though the reaction rate is improved by lowering the water content, the oxidation reaction goes reasonably well at increased water concentrations in the reaction mixture. The results of experiments 25 and 9 indicate that bromine and hydrobromic acid are substantially equivalent as catalysts at substantially the same water levels in the reaction mixture. In experiment 9, water was present in the concentrated hydrobromic acid catalyst. However, in experiment 25, water was added to the reaction mixture to adjust the water content to substantially the same level as in experiment 9.

EXAMPLE II

A solution of 60 ml of 2-methyl-2-propanethiol (0.522 mole) and 2.0 ml of 48 percent hydrobromic acid (0.0178 mole) in 90 ml of DMSO (1.27 mole) was heated with stirring under reflux with a bath at 65°C. At the level of thiol reactant which was used, boiling and an exothermic reaction set in after about 15 minutes. The reaction vessel was cooled until the reaction subsided, and then heating at 65°C. was continued. After half an hour, 1 drop of reaction mixture would not de-colorize 1 ml of a 0.025 percent solution of iodine in DMSO. The mixture (two phases present) was allowed to cool a bit, and then dimethyl sulfide was removed by distillation at 150 mm of Hg into a receiver cooled with acetone-dry ice. The distillate, 12.3 g (76 percent of theory), was treated with anhydrous potassium carbonate to remove a trace of water and was then redistilled at atmospheric pressure. Bp, 37°–9°C., Reported Bp for dimethyl sulfide, 38°C. Treatment with alcoholic $HgCl_2$ gave the mercuric chloride derivative having a Mp of 158°–60°C. (reported, 156°–8°C.).

The undistilled portion of the reaction mixture was treated with 60 ml of water and the organic phase was removed and extracted with another 60 ml of water. The aqueous phases were combined and then extracted with 60 ml of ethyl ether. The ether phase was then extracted with an equal volume of water and this ether phase was combined with the organic phase and dried over anhydrous potassium carbonate. Distillation of the dried solution gave 40.6 g (87 percent of theory) of bis(t-butyl) disulfide. Bp, 89°–90°C./22 mm (reported, 88°C./21 mm). Mp, −6° to −2°C. (reported, −4.95°C.). $n_D^{25}$ 1.4872 (reported, $n_D^{20}$ 1.4899).

EXAMPLE III

A number of experiments were carried out under the same general conditions as described in Example I with the exception that the sulfoxide reactant was tetramethylene sulfoxide. The results of these experiments are set forth in Table IV in which the catalyst is indicated and the catalyst concentration is expressed in mole percent based on the sulfoxide reactant. The reaction temperature is expressed in degrees centigrade and the completion times for the various reactions are expressed in hours.

TABLE IV

Oxidation of 2-methyl-2-propanethiol to Bis(t-butyl) disulfide by Tetramethylene Sulfoxide

| Catalyst | Cat. Concen. | Temperature | Completion Time |
|---|---|---|---|
| $I_2$ | 1.55 | 65°C. | 0.1* |
| $I_2$ | 1.55 | 50 | 0.4 |
| $I_2$ | 1.55 | 25 | 9.5 |
| HI | 1.55 | 50 | 0.8 |

TABLE IV-continued

Oxidation of 2-methyl-2-propanethiol to Bis(t-butyl) disulfide by Tetramethylene Sulfoxide

| Catalyst | Cat. Concen. | Temperature | Completion Time |
|---|---|---|---|
| $Br_2$ | 1.64 | 25 | 0.1* |
| HBr | 1.60 | 50 | 0.1* |
| HBr | 1.60 | 25 | 0.3 |
| HCl | 3.22 | 50 | 7.0 |
| $CH_3SO_3H$ | 3.18 | 50 | $NAR_{14}$ |

*Noticeably exothermic

As shown above, the completion time for the oxidation reaction is temperature dependent with an increase in the reaction temperature resulting in a shortened completion time. Also, as indicated, the use of a strong acid, i.e., methane sulfonic acid, had no apparent effect as a catalyst and no reaction was observable in use of this acid after heating for 14 hours at 50°C. In the experiments reported in Table IV, the mole ratio of thiol to sulfoxide was 0.47.

EXAMPLE IV

A solution of 18 ml of 2-methyl-2-propanethiol (0.157 mole) and 0.66 g of iodine (0.0052 mole as HI) in 30 ml of tetramethylene sulfoxide was cautiously heated at 50°C. until a deep amber color appeared (about half an hour). After it was cool (two liquid phases present), the mixture was shaken with 50 ml of water containing sodium carbonate until the amber color disappeared. The aqueous phase was then removed and the organic phase was extracted twice with 25 ml of water. The aqueous extracts were combined and extracted three times with 20 ml portions of ethyl ether. The ether extracts were then combined with the original organic phase and treated with anhydrous potassium carbonate. Distillation of the thus dried solution gave 5.8 g of tetramethylene sulfide (84 percent of theory). Bp, 119°–21°C. (reported, 119°–22°C. The mercuric chloride derivative melted at 128°–31°C. (reported, 125°–6°C.). Further distillation gave 11.4 g of bis(t-butyl) disulfide (82 percent of theory). Bp, 88°–9°C./22 mm (reported, 88°C./21 mm). Mp, −6° to −2°C. (reported, −4.95°C.).

EXAMPLE V

Several experiments were carried out using the general reaction conditions of Example I with the exception that dipropyl sulfoxide was employed as the sulfoxide reactant. The results of these reactions are set forth in Table V in which the catalyst and catalyst concentration are indicated in the same manner as described previously with the reaction temperature set forth in degrees centigrade and the completion time in hours. During the course of these experiments, there was no separation of the disulfide product phase. In these experiments, the molar ratio of thiol to sulfoxide was 0.49.

TABLE V

Oxidation of 2-methylpropane-2-thiol to Bis(t-butyl) disulfide by Dipropyl Sulfoxide

| Catalyst | Cat. Concen. | Temperature | Completion Time |
|---|---|---|---|
| $I_2$ | 1.62 | 50°C. | 1.5 |
| HBr | 1.66 | 50 | 0.8 |
| HCl | 3.36 | 65 | 8.8 |
| $CH_3SO_3H$ | 3.31 | 65 | $NAR_{20}$ |

As shown in Table V, hydrobromic acid was the most effective of the catalysts and its usage gave the shortest completion time. Also, the presence of methane sulfonic acid in the reaction mixture was found to have no discernible catalytic effect.

EXAMPLE VI

A further series of experiments were carried out in the general manner indicated in Example I with the exception that the thiol reactant was 1-dodecanethiol. The mole ratio of the thiol reactant with respect to the sulfoxide reactant was 0.40 except where indicated to the contrary. Neither the thiol reactant nor the disulfide product were completely soluble in dimethyl sulfoxide. Thus, two phases were present at all times and the disulfide product crystallized from the thiol-disulfide phase on cooling.

TABLE VI

Oxidation of 1-Dodecanethiol to Didodecyl disulfide by DMSO

| Catalyst | Cat. Concen. | Temperature | Completion Time (hrs.) |
|---|---|---|---|
| $I_2$ | 1.24 | 75°C. | 1.7 |
| $I_2$ | 1.24 | 60 | 8.8 |
| HBr | 1.40 | 75 | 1.0 |
| HBr | 1.40 | 60 | 2.2 |
| HCl | 1.42 | 75 | 4.5** |
| $CH_3SO_3H$ | 1.39 | 75 | $NAR_{10}$** |
| $HCl + I_2$ | 0.95 & 0.0680 resp. | | 1.2 |
| $CH_3SO_3H + I_2$ | 1.39 & 1.24, | 60 | 3.5 |

**Mole ratio of thiol to DMSO, 0.20.

As illustrated in Table VI, the completion times were shortened as the reaction temperature was increased and were also affected by the particular catalyst which was employed. The presence of a small quantity of iodine was found to greatly enhance the catalytic effect of hydrochloric acid as the primary catalyst and, the presence of a strong acid, methanesulfonic acid, was found to provide some improvement in the use of iodine as the primary catalyst. In addition, it was found that methanesulfonic acid was ineffective under the reaction conditions employed and no apparent reaction was discerned after heating for 10 hours at a temperature of 75°C.

EXAMPLE VII

A mixture of 9 ml of DMSO (127 mmole), 12 ml of 1-dodecanethiol (50 mmole), 0.1 ml of 37 percent hydrochloric acid (1.2 mmole), and 10.8 mg of iodine (0.085 mmole as HI) was heated by a bath, while stirring magnetically, at about 60°C. After one and a fourth hours, the lower phase became amber colored. The mixture was cooled with stirring to produce fine crystals. These were filtered off and rinsed with DMSO. Recrystallization from acetone gave 9.02 g of didodecyl disulfide (90 percent of theory). Mp, 33°–5°C. (reported, 33°–4°C.).

EXAMPLE VIII

A further series of reactions were conducted in the manner described previously in Example I except that the thiol reactant was α-toluenethiol. The reactions were carried out at a temperature of 60°C. and the mole ratio of the thiol reactant with respect to the dimethyl sulfoxide reactant was 0.40. The desired dibenzyl disulfide product was crystallized from the reaction mixture on cooling and could be recovered by first removing dimethyl sulfide by evaporation at reduced pressure and then completing the precipitation by addition of water. The recovered crude product was recrystallized from 95 percent ethyl alcohol and the yield was about 93 percent of theory, Mp, 70°-3°C. (reported, 71°-2°C.).

TABLE VII

| Catalyst | Oxidation of α-Toluenethiol by DMSO | |
|---|---|---|
| | Cat. Concen. as HX | Completion Time (hrs.) |
| $I_2$ | 1.36 | 1.6 |
| HBr | 1.40 | 0.9 |
| HCl | 1.42 | 1.7* |
| $CH_3SO_3H$ | 1.39 | $NAR_9$* |

*Mole ratio of thiol to DMSO, 0.20.

As shown by the data in Table VII, the oxidation of α-toluenethiol responds favorably to catalysis by iodine, hydrobromic acid and hydrochloric acid. Thus, it closely resembles the oxidation of the aliphatic thiols rather than the aromatic thiols which are readily oxidized by a sulfoxide in an acidic environment and show only a similar response to halogen-hydrogen halide catalysis. Also, α-toluenethiol closely resembles the aliphatic thiols in terms of the time and temperature conditions required for completion of the oxidation reaction. As indicated in the above Table, methanesulfonic acid was found to have no discernible catalytic effect upon the desired oxidation and no apparent reaction was indicated after 9 hours of heating at 60°C.

EXAMPLE IX

A solution of 4.5 ml of 1,4-butane dithiol (39.3 mmole) and 0.16 g of iodine (1.26 mmole as HI) in 13.5 ml of DMSO (191 mmole) was heated with stirring at 65°C. under a deep amber color appeared (about 10 hours). A solution of 0.16 g of potassium carbonate in 25 ml of water was then stirred in to remove iodine. This mixture was extracted three times with ether. An aqueous phase and rubbery poly(1,4-butylene disulfide) remained. The combined ether extracts were treated with a small amount of decolorizing carbon and then filtered. Ether was evaporated and the residue was iced. That portion which did not crystallize was pipetted off and discarded. Yield of 1,2-dithian was 2.54 g (54 percent of theory). After further purification by fractional freezing, Mp was 31°-2°C. (reported 32°-3°C.).

EXAMPLE X

A solution of 4.5 ml of 1,4-butanedithiol in 3.5 ml of DMSO was added to a stirred solution of 0.16 g of iodine in 10 ml of DMSO at 65°C. at such a rate that the iodine color was just discharged. Seventeen hours were required to complete this addition. Once the final iodine color appeared, aqueous potassium carbonate was added, and the mixture further treated as described in the above example. Three and six hundredths g of 1,2-dithian (65 percent of theory) was thus obtained.

The results set forth in Examples IX and X demonstrate the effect of gradual addition of the thiol reactant upon the yield of the desired cyclic disulfide product, 1,2-dithian. In Example IX, where the dithiol reactant was not added gradually, a reduced yield of the desired cyclic disulfide product was obtained. However, by slowly adding the dithiol reactant to the reaction mixture, as in Example X, the yield of the cyclic disulfide dithian product was increased to 65 percent of theory.

As indicated, gradual addition of the dithiol reactant favors formation of the cyclic disulfide product while abrupt addition of the dithiol reactant favors formation of the polymeric disulfide product.

EXAMPLE XI

To a stirred solution of 0.30 ml of 37 percent hydrochloric acid (3.6 mmole) and 0.22 g of iodine (1.73 mmole as HI) in 9 ml of DMSO (127 mmole), 4 ml of thioacetic acid (57.4 mmole) was added at such a rate that the mixture always had some iodine color. One and a half hours were required for addition. When the amber, iodine color was finally full, a solution of 0.75 g of potassium carbonate in 30 ml of water was stirred in to remove iodine. This mixture was extracted three times with 35 ml of ether. The combined extracts were dried over 4A molecular sieves, and then the ether was removed by evaporation. Filtration removed a small amount of sulfur from the product, diacetyl disulfide. The weight of product was 3.24 g (75 percent of theory). After purification by fractional freezing, Mp was 15°-8°C. (reported, 20°C.).

As illustrated by the foregoing specification and examples, the present process provides a greatly improved oxidation of thiols to disulfides. This permits the use of shorter reaction times and also permits conducting the oxidation at lower reaction temperatures which have less tendency to decompose the reactants. In addition, the present process permits the oxidation of thiol reactants in which a carbonyl group joins the —SH group to the R group, such as thioacetic acid, or the oxidation of thiols in which a tertiary carbon atom is connected to the thiol group, e.g., 2-methyl-2-propanethiol. Such thiols have previously been very difficult to oxidize to disulfides using sulfoxides.

The preferred sulfoxide reactants, as defined hereiin, are represented by the formula

where R' and R'' are lower alkyl groups such as methyl or hexyl. Also, however, other sulfoxide compounds containing the (S=O) moiety may be employed as oxidants as disclosed in U.S. Pat. No. 3,376,313, which is incorporated herein by reference.

The disulfide products produced by the present process are known materials that have know utilities. Thus, as disclosed in U.S. Pat. No. 3,376,313, disulfides are useful as additives in cosmetic products and depilatory creams.

I claim:

1. A process for the formation of a disulfide through oxidation of a thiol, said process comprising:
   reacting a thiol having the formula R-SH or

with a sulfoxide having the formula

in the presence of a catalytically effective amount of a halogen or hydrogen halide catalyst in which the halogen or hydrogen halide catalyst is iodine, bromine, chlorine, hydrogen iodide, hydrogen bromide, hydrogen chloride, or mixtures thereof, with R being an alkyl group containing from 1 to about 20 carbon atoms, a cycloaliphatic group containing from 3 to about 20 carbon atoms, an aralkyl group containing from 5 to about 20 carbon atoms, or a mixture of such groups, R' and R'' being lower alkyl groups which may be the same or different and may be bonded together to form a ring structure, said reaction being carried out at a temperature of less than about 100°C. to prevent oxidation of the disulfide product to a sulfonic acid, and discontinuing the reaction when the oxidation of said thiol to a disulfide is substantially completed.

2. The process of claim 1 wherein said reaction is carried out at a temperature of 75°C. or less.

3. The process of claim 1 wherein the sulfoxide reactant is dimethyl sulfoxide.

4. The process of claim 1 wherein the sulfoxide reactant is tetramethylene sulfoxide.

5. The process of claim 1 wherein the sulfoxide reactant is dipropyl sulfoxide.

6. The process of claim 1 wherein said sulfoxide is present in a stoichiometric excess in the reaction mixture.

7. The process of claim 1 in which the catalyst is a mixed catalyst comprising chlorine or hydrogen chloride as the primary catalyst and iodine or hydrogen iodide as a secondary catalyst.

8. The process of claim 1 wherein the R group is substituted with more than one thiol group.

9. The process of claim 8 wherein the thiol reactant is 1,4-butanedithiol.

10. The process of claim 1 wherein the R-SH reactant is a mixture of thiols or thiol carbonyls to product disulfide products containing mixed R groups or mixed

groups.

11. The process of claim 1 wherein the thiol reactant contains a tertiary carbon atom which is bonded to the —SH group.

12. The process of claim 11 wherein the thiol reactant is 2-methyl-2-propanethiol.

13. The process of claim 1 wherein the thiol reactant is a thiol carbonyl having the formula

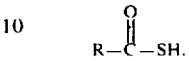

14. The process of claim 12 wherein the thiol reactant is thioacetic acid.

15. The process of claim 1 wherein the thiol reactant is 1-dodecanethiol.

16. The process of claim 1 wherein said sulfoxide is present in a molar excess of about 100 percent with respect to said R—SH or

reactant.

17. The process of claim 16 wherein said catalyst is a mixed catalyst containing chlorine or hydrogen chloride as a primary catalyst and iodine or hydrogen iodide as a secondary catalyst.

18. The process of claim 1 wherein the reaction mixture contains iodine or hydrogen iodide and the reaction is conducted until the reaction mixture takes on an amber coloration.

19. The process of claim 1 including the step of maintaining the water content of the reaction mixture at a relatively low level.

20. The process of claim 1 including the step of agitating the reaction mixture.

21. The process of claim 1 wherein the acidity of the reaction mixture is increased by the inclusion of an acid which is not a hydrohalic acid.

22. The process of claim 1 wherein R is an aralkyl group.

23. The process of claim 22 wherein the thiol reactant is α-toluenethiol.

* * * * *